United States Patent
Jin

(10) Patent No.: US 11,890,314 B1
(45) Date of Patent: Feb. 6, 2024

(54) PHARMACEUTICAL COMPOSITION FOR TREATING, PREVENTING OR AMELIORATING SPINAL MUSCULAR ATROPHY AND ADMINISTRATION METHOD THEREOF

(71) Applicant: NOVEL PHARMA INC., Seoul (KR)

(72) Inventor: Dong Kyu Jin, Seoul (KR)

(73) Assignee: NOVEL PHARMA INC., Seoul (KR)

( * ) Notice: Subject to any disclaimer, the term of this patent is extended or adjusted under 35 U.S.C. 154(b) by 0 days.

(21) Appl. No.: 17/813,480

(22) Filed: Jul. 19, 2022

(51) Int. Cl.
| | |
|---|---|
| *A61K 38/17* | (2006.01) |
| *A61P 21/00* | (2006.01) |
| *A61K 9/00* | (2006.01) |
| *A61K 38/01* | (2006.01) |
| *A61P 19/00* | (2006.01) |
| *A61K 47/54* | (2017.01) |

(52) U.S. Cl.
CPC .......... *A61K 38/012* (2013.01); *A61K 9/0021* (2013.01); *A61K 38/1709* (2013.01); *A61K 47/548* (2017.08); *A61P 19/00* (2018.01); *A61P 21/00* (2018.01)

(58) Field of Classification Search
CPC ............ A61K 38/17; A61K 9/00; A61P 21/00
See application file for complete search history.

(56) References Cited

U.S. PATENT DOCUMENTS

2011/0190216 A1* 8/2011 Calvin ................... A61P 25/00
514/17.7
2018/0312839 A1* 11/2018 Bhat .................... C12N 15/113

OTHER PUBLICATIONS

Chaytow et al., Cell Mol. Life Sci., 2018, vol. 75(21):3877-3894.*
Cohen-Pfeffer et al., Pediatric Neurology, 2017, vol. 67:23-35.*
Wurster et al., Ther. Adv. in Neurol. Disord., 2018, vol. 11:1-3.*

* cited by examiner

*Primary Examiner* — Xiaozhen Xie
(74) *Attorney, Agent, or Firm* — Sughrue Mion, PLLC

(57) ABSTRACT

The present disclosure relates to a pharmaceutical composition for treating, preventing and/or ameliorating spinal muscular atrophy (SMA) and a method of administration thereof. A pharmaceutical composition for treating, preventing and/or ameliorating SMA according to an embodiment of the present disclosure may comprise a SMN protein, which is the cause of the onset of SMA. The pharmaceutical composition may be administered directly to a subject suffering from SMA via intracerebroventricular, intrathecal or intra-cisterna magna administration, thereby treating or preventing SMA or ameliorating symptoms of SMA. The pharmaceutical composition for treating, preventing or ameliorating SMA according to one embodiment of the present disclosure is safe, cost-effective and/or accessible compared to other previously approved drugs and can achieve substantially equivalent therapeutic effects.

8 Claims, 6 Drawing Sheets

Specification includes a Sequence Listing.

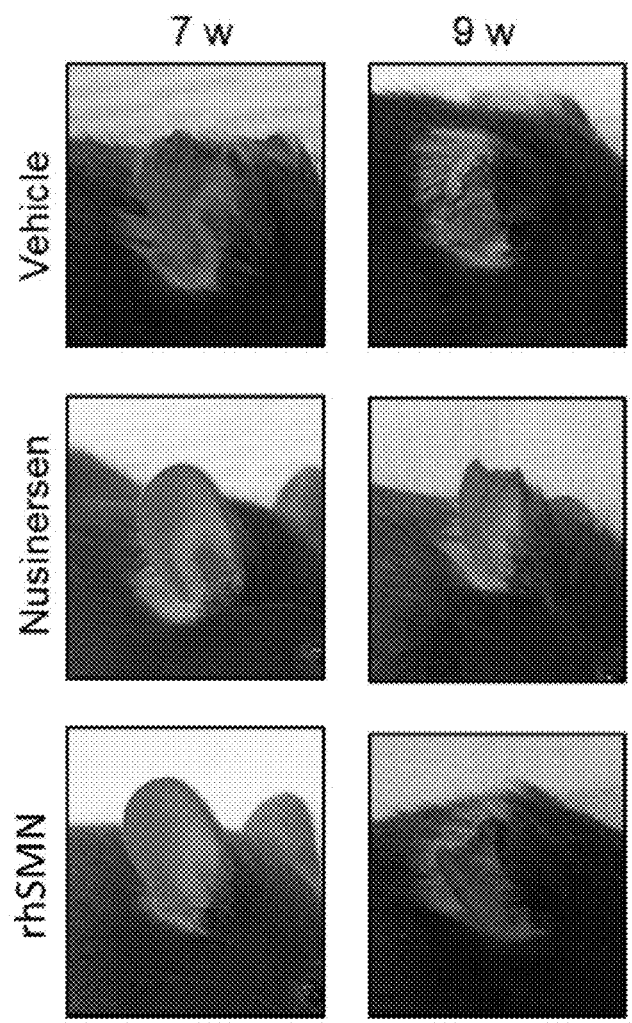

PHARMACEUTICAL COMPOSITION FOR TREATING, PREVENTING OR AMELIORATING SPINAL MUSCULAR ATROPHY AND ADMINISTRATION METHOD THEREOF

FIELD OF THE APPLICATION

The present disclosure relates to pharmaceutical compositions for treating, preventing or ameliorating spinal muscular atrophy and methods of administration thereof.

BACKGROUND

Spinal muscular atrophy (SMA) is a genetic, neurodegenerative disease caused by the gradual death of motor neuron cells as the number of survival motor neuron (SMN) proteins, which are required for the survival of motor neuron cells, decreases. SMA is caused by mutations in the survival motor neuron 1 (SMN1) gene encoding the SMN protein in humans. SMN2 gene also encodes the SMN protein, but single nucleotide polymorphism of the SMN2 gene compared to the SMN1 gene disrupts the binding of splicing modifiers and results in a truncated, unstable protein that cannot oligomerize efficiently and is rapidly degraded. SMA is often diagnosed in infancy or early childhood and, if untreated, eventually leads to death before the second year of age due to dyspnea caused by weakening of respiratory muscles. SMA is an early-onset, autosomal recessive disease with a high prevalence rate of 1 in 6,000 to 10,000 newborns (with a carrier frequency of approximately 1 in 35) and is the most common genetic cause of infant mortality in the United States and a major cause of child morbidity.

SMA is generally characterized by muscle weakness and atrophy predominating in proximal limb muscles and exhibits a range of phenotypes, which are classified into four major types that depend on the age of onset and the motor abilities. Type I SMA (infant-onset SMA or Werdnig-Hoffmann disease), accounting for approximately 50-60% of all SMA, is the most severe form of the disease that develops at birth or within 6 months after birth, and life expectancy of untreated infants is less than two years. Type I SMA patients in general cannot sit or walk. Late-onset SMA can be categorized into type II SMA and type III SMA (Kugelberg-Welander disease). Type II SMA is usually diagnosed after 6 months but before 18 months of age and shows intermediate severity. The patients of Type II SMA can sit but cannot stand or walk on their own and, if untreated, are expected to die around the age of 6-7. Type III SMA patients typically show their symptoms after 18 months of age. These patients can walk independently but often develop scoliosis, and if they lose their walking ability, the patients may develop obesity or osteoporosis. Adult-onset or type IV SMA develops after the age of 18 and usually causes mild motor impairment. Type IV patients can walk but may have complications such as scoliosis or articular rigidity and/or exhibit muscle weakness after age 30. Type IV patients have normal life expectancy.

Various methods have been attempted to treat SMA, such as administering viral vectors expressing SMN proteins into the body (gene therapy), administering novel compounds that act as an SMN2 splice modulator, or administering antisense oligonucleotides that regulate splicing of SMN2 mRNA to increase the production of SMN proteins in the body (RNA injection). However, methods of introducing a foreign gene using a viral vector have not established sufficient safety yet. In addition, drugs targeting the splicing machinery may affect other transcripts, resulting in unknown off-target side effects, and may affect cell division and cause oncogenic side effects. Further, RNA injections or gene therapies have limitations as these treatments are not widely available for many patients partly due to high costs. Therefore, there is a need in the art to develop compositions and methods that are capable of effectively treating, preventing or ameliorating SMA in a safer and more cost-efficient way.

SUMMARY

The present disclosure is related to a pharmaceutical composition for treating, preventing and/or ameliorating SMA or at least one of its symptoms. In one embodiment of the present disclosure, the pharmaceutical composition may comprise SMN protein or recombinant SMN protein. In one embodiment, the pharmaceutical composition may be configured to be administered via intracerebroventricular (ICV) injection, intrathecal (IT) injection, intra-cisterna magna (ICM) administration, intraparenchymal injection, intracerebral (IC) injection, intravenous (IV) injection or a combination thereof. In one embodiment, the pharmaceutical composition may be configured to be administered via a combination of ICV injection and IV injection. In one embodiment, the pharmaceutical composition may be safe, cost-effective and/or accessible compared to other previously approved drugs or pharmaceutical compositions for treating, preventing or ameliorating SMA but may achieve substantially equivalent therapeutic effects.

The present disclosure provides SMN protein or recombinant SMN protein for use in the treatment, prevention and/or amelioration of SMA or at least one of its symptoms. In one embodiment, the SMN protein or recombinant SMN protein may be configured to be administered ICV, IT, ICM, intraparenchymal, IC, IV or a combination thereof. In one embodiment, the SMN protein or recombinant SMN protein may be safe, cost-effective and/or accessible compared to previously approved drugs or pharmaceutical compositions for treating, preventing or ameliorating SMA but may achieve substantially equivalent therapeutic effects.

The present disclosure provides a method of treating, preventing and/or ameliorating SMA or at least one of its symptoms. In one embodiment of the present disclosure, the method may comprise a step of administering, delivering or supplying to a patient with SMA a pharmaceutical composition comprising SMN protein or recombinant SMN protein via ICV, IT, ICM, intraparenchymal, IC, IV administration or injection, or a combination thereof. In one embodiment, the method may treat or prevent SMA or ameliorate the symptoms in patients with SMA. In one embodiment, the method may be safer, more cost-effective and/or accessible to patients than a method for treating, preventing or ameliorating SMA that comprises a step of administering other previously approved drugs or pharmaceutical compositions for treating SMA but may achieve substantially equivalent therapeutic effects. According to one embodiment of the present disclosure, as the method shows its therapeutic effects earlier than currently available treatments for patients with SMA, the method may be used as an early, adjunctive treatment to currently available treatments for patients with SMA or a treatment for patients with early-onset SMA.

In one embodiment, the present disclosure may be related to a method of treating, preventing or ameliorating SMA comprising: administering to a patient with SMA a therapeutically effective amount of a pharmaceutical composition comprising a SMN protein via an ICV administration, an IT administration, an ICM administration, an intraparenchymal injection, an IC injection, an intravenous IV injection or a combination thereof, wherein after the administration of the therapeutically effective amount of the pharmaceutical composition, at least one symptom of SMA is reduced in intensity, severity or frequency, or has delayed onset.

In one aspect, the SMN protein may be encoded by human SMN1 gene.

In one aspect, the SMN protein may comprise an amino acid sequence having at least 90% sequence identity to the amino acid sequence of SEQ ID NO: 1.

In one aspect, the SMN protein may comprise the amino acid sequence of SEQ ID NO:1.

In one aspect, the SMN protein may be a recombinant human SMN protein.

In one aspect, the patient with SMA may be a patient with SMA type I, SMA type II, SMA type III or SMA type IV.

In one aspect, administering to the patient with SMA the therapeutically effective amount of the pharmaceutical composition may comprise administering to the patient with SMA the therapeutically effective amount of the pharmaceutical composition once a week, once every two weeks, twice a month or once a month.

In one aspect, the ICV administration may comprise administering to the patient with SMA the therapeutically effective amount of the pharmaceutical composition in one or more cerebral ventricles.

In one aspect, the ICV administration may comprise administering to the patient with SMA the therapeutically effective amount of the pharmaceutical composition via an intraventricular catheter system comprising a reservoir and a catheter connected to the reservoir.

In one aspect, administering to the patient with SMA the therapeutically effective amount of the pharmaceutical composition may comprise administering to the patient with SMA the pharmaceutical composition in a dose of about 0.0001 mg/kg to about 150 mg/kg.

In one aspect, the pharmaceutical composition is administered in combination with SPINRAZA®.

In one embodiment, the present disclosure may be related to a pharmaceutical composition for treating, preventing or ameliorating spinal muscular atrophy, comprising a SMN protein, wherein the pharmaceutical composition is administered via an ICV administration, an IT administration, an ICM administration, an intraparenchymal injection, an IC injection, an IV injection or a combination thereof.

In one aspect, the SMN protein is encoded by human SMN1 gene.

In one aspect, the SMN protein may comprise an amino acid sequence having at least 90% sequence identity to the amino acid sequence of SEQ ID NO:1.

In one aspect, the SMN protein may comprise the amino acid sequence of SEQ ID NO:1.

In one aspect, the SMN protein may be a recombinant human SMN protein.

In one aspect, the patient with SMA may be a patient with SMA type I, SMA type II, SMA type III or SMA type IV.

In one aspect, the pharmaceutical composition may be administered once a week, once every two weeks, twice a month or once a month.

In one aspect, the ICV administration may comprise administering the pharmaceutical composition in one or more cerebral ventricles.

In one aspect, the ICV administration may comprise administering via an intraventricular catheter system comprising a reservoir and a catheter connected to the reservoir.

In one aspect, the SMN protein may be administered in a dose of about 0.0001 mg/kg to about 150 mg/kg.

In one aspect, the pharmaceutical composition may further comprise a pharmaceutically acceptable carrier.

In one aspect, the pharmaceutical composition may be administered in combination with SPINRAZA®.

BRIEF DESCRIPTION OF THE DRAWINGS

FIG. 3 shows the mouse brain (A) right after ICV administration of Trypan Blue, (B) 15 minutes after administration and (C) 24 hours after administration.

FIG. 2 illustrates the change in tail length of SMA mice treated with vehicle, Nusinersen and rhSMN protein over time (in days after birth).

FIG. 5 illustrates the timing of ear necrosis (in weeks of age) in SMA mice treated with vehicle, Nusinersen and rhSMN protein.

FIG. 6 shows pictures of ear necrosis in SMA mice over time (in weeks of age). More specifically, FIG. 6 illustrates ear necrosis in SMA mice treated with vehicle, Nusinersen and rhSMN protein in 7 and 9 weeks of age.

DETAILED DESCRIPTION

Figure 1:
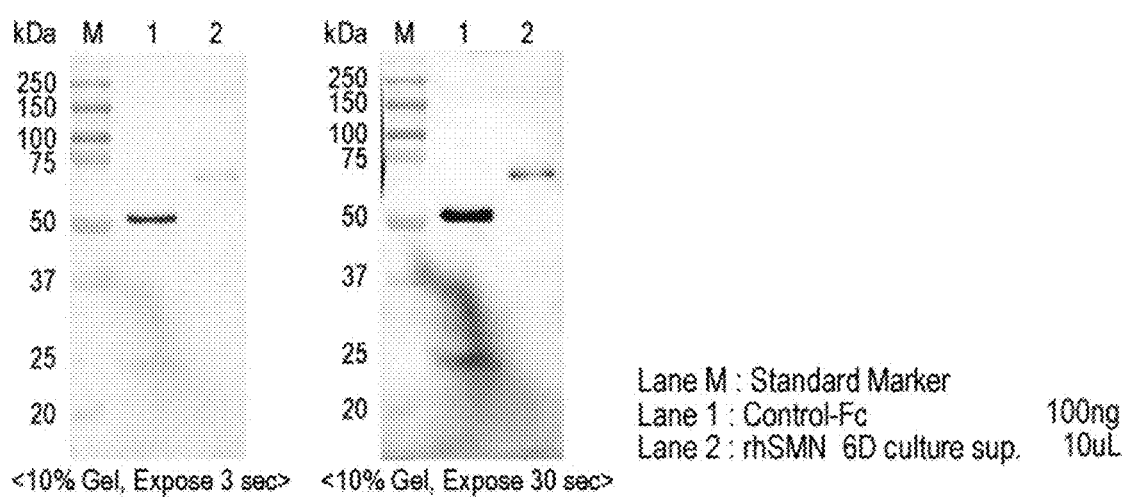
FIG. 1 shows the Western blot result of the cell culture supernatant of 293F cells expressing recombinant human SMN (rhSMN) protein on the sixth day of incubation.

Various embodiments or examples of the present disclosure are for the purpose of illustrating and/or explaining the present application and are not intended to be limiting. The present disclosure include various modifications, equivalents and/or alternatives of each embodiment or example described in this application and/or any possible combinations of all or part of each embodiment or example described in this application. The scope of rights of the present disclosure is not limited to various embodiments or examples set forth below or the specific descriptions of the embodiments or examples.

All technical and scientific terms used in this application, unless otherwise defined, generally have the ordinary meanings understood by a person of ordinary skill in the art to which this disclosure pertains. All terms used in this application are chosen for the purpose of describing and/or explaining this disclosure and are not intended to limit the scope of rights under this disclosure. Certain terms are discussed in this application to provide additional guidance in describing and/or explaining the compositions and method of the present disclosure.

Definitions

Whenever used in the present disclosure, the singular forms "a," "an" and "the" and singular words include plural reference unless the context clearly dictates otherwise, and the same shall apply to the singular forms and words set forth in the claims. For example, "a compound" includes a plurality of such compounds, and "a compound A" includes a plurality of compounds A.

The term "and/or" means any one or more of the items, any combination of the items, or all of the items with which this term is associated. The terms "containing," "contain," "contains," "including," "include," "includes," "having," "have," "has," "with" or variants thereof are interpreted as inclusive in a manner similar to the term "comprising."

All ranges recited in this application may include any and all possible subranges and combinations of subranges thereof. A recited range includes each specific value, integer or decimal within the ranges. One of ordinary skill in the art may readily understand that any recited range sufficiently describes and/or enables its subranges, including and not limited to equal halves, thirds, quarters, fifths or tenths of the recited range.

The terms "greater than," "more than," "at least," "or more," "less than," "up to" and the like, include the numbers recited, and the terms refer to ranges that may be broken down into subranges as discussed above. Specific values recited for ranges are for illustration purposes only and are not intended to be limiting, and they do not exclude other values within the ranges.

Unless indicated otherwise, the term "about" and "approximately" generally include values proximate to the recited range or value within an acceptable degree of error, as well known to those skilled in the art. The acceptable degree of error may be determined in view of the nature or precision of the measurements. In one embodiment, the acceptable degree of error may be determined based on equivalence in terms of the functionality of the composition or method or the embodiment. In one embodiment, in the context of numerical values or ranges set forth in this disclosure, the term "about" or "approximately" can refer to a variation of ±25%, ±20%, ±15%, ±10%, ±9%, ±8%, ±7%, ±6%, ±5%, ±4%, ±3%, ±2% or ±1% of the value provided. In another embodiment, particularly in biological systems, the terms "about" and "approximately" may mean values that are within an order of magnitude, within 9-fold, 8-fold, 7-fold, 6-fold, 5-fold, 4-fold, 3-fold or 2-fold of a given value. All numerical quantities provided in this application are approximations unless stated otherwise. In addition, these quantities inherently contain variability necessarily resulting from their measurements.

In the present disclosure, the term "pharmaceutical composition" may refer to a form of a pharmaceutical preparation that allows the biological activity of an active ingredient contained in the composition to be effective. In one embodiment, the pharmaceutical composition is a composition comprising one or more active ingredients that can be administered to a patient and does not further comprise an unacceptable toxic component.

In the present disclosure, the term "pharmaceutically acceptable" may refer to a property of substance that is useful for the preparation of generally safe, non-toxic and biologically or otherwise desirable pharmaceutical compositions and is acceptable for human pharmaceutical applications and/or veterinary applications. In one embodiment, the term "pharmaceutically acceptable" means approved or approvable by a government regulatory agency or listed in generally recognized pharmacopoeia for use in humans and/or animals.

In the present disclosure, the term "pharmaceutically acceptable excipient" refers to any component that is not therapeutically active (inert) and non-toxic. In one embodiment, the pharmaceutically acceptable excipient may include, but is not limited to, for example, a binder, filler, solvent, buffer, tonicity agent, stabilizer, antioxidant, surfactant or lubricant configured to be used in formulating a pharmaceutical product.

As used herein, the term "pharmaceutically acceptable carrier" refers to a component of a pharmaceutical composition other than an active ingredient, the component being non-toxic to a subject. In one embodiment, the pharmacologically acceptable carrier may include, but is not limited to, for example, a buffer, excipient, stabilizer or preservative.

In the present disclosure, the terms "pharmaceutically effective dose," "pharmaceutically effective amount," "administration dose," "administration amount," "therapeutically effective dose," "therapeutically effective amount," "effective dosage" or "effective amount" of a pharmaceutical composition may refer to an amount of a pharmaceutical composition (to be administered for the required duration) that is sufficient to achieve a therapeutic response or effect, a desired local or systemic therapeutic result or a desired preventive result. In one embodiment, the above terms refer to an amount of a pharmaceutical composition that, when administered to a subject, (i) treats or prevents, (ii) mitigates, reduces, ceases, attenuates, ameliorates or eliminates one or more symptoms of, or (iii) prevents or delays the onset of one or more symptoms of the disease, condition or disorder described herein (e.g., SMA).

In the present disclosure, the term "subject" refers to a mammal. Mammals may include, but are not limited to, domesticated animals (e.g., cows, sheep, cats, dogs, and horses), primates (e.g., human and non-human primates, such as monkeys), rabbits and rodents (e.g., mice and rats). In one embodiment, the subject may be a human. In one embodiment, the subject may be a human with SMA. In another embodiment, the subject may be a human suffering from SMA, which is caused by an inactivating mutation or deletion of the SMN1 gene on two chromosomes, resulting in loss of the SMN1 gene function.

In the present disclosure, the term "spinal muscular atrophy" (SMA) relates to a disease caused by an inactivating mutation or deletion of the SMN1 gene on two chromosomes, resulting in loss of SMN1 gene function. Symptoms of SMA may include muscle weakness, poor muscle tone, weak cry, weak cough, limpness or a tendency to flop, difficulty sucking or swallowing, difficulty breathing, accumulation of secretions in the lungs or throat, clenched fists with sweaty hands, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

In the present disclosure, the term "treating spinal muscular atrophy (SMA)" or "treatment of spinal muscular atrophy (SMA)" may include one or more of the following effects: (i) reducing or ameliorating the severity of SMA; (ii) delaying the onset of SMA; (iii) inhibiting the progression of SMA; (iv) reducing the subject's hospitalization; (v) reducing the length of the subject's hospitalization; (vi) increased survival of the subject; (vii) improved quality of life of the subject; (viii) reduced number of symptoms associated with SMA; (ix) reduced or ameliorated severity of one or more symptoms associated with SMA; (x) reduction in the duration of symptoms associated with SMA; (xi) prevention of recurrence of symptoms associated with SMA; (xii) inhibiting the development or onset of symptoms of SMA; and/or (xiii) inhibiting the progression of symptoms associated with SMA.

In this disclosure, "treating SMA" or "treatment of SMA" can represent one or more of the following beneficial effects: (i) reduction in muscle strength loss; (ii) increase in muscle strength; (iii) reduction in muscular atrophy; (iv) reduction in loss of motor function; (v) increase in motor neurons; (vi) reduction in motor neurons loss; (vii) protection of SMN deficient motor neurons from degeneration; (viii) increase in motor function; (ix) increase in pulmonary function; and/or (x) reduction in pulmonary function loss.

In the present disclosure, "treating SMA" or "treatment of SMA" refers to (i) the functional ability or retention of the functional ability of a human infant or a human toddler to sit up without help, or (ii) the functional ability or retention of the functional ability of a human infant, a human toddler, a human child or a human adult to stand up without help, walk without help, run without help, breathe without help, turn during sleep without help or swallow without help.

The terms "prevention" or "preventing" of a disease state may refer to a reduction in risk of acquiring a disease, condition or disorder or causing at least one of the clinical symptoms of the disease not to develop in a subject that may be exposed to or predisposed to the disease but does not yet experience or display symptoms of the disease.

In one embodiment of the present disclosure, the term "recombinant human SMN protein" or "rhSMN protein" may refer to protein expression products obtained by expressing human SMN protein via genetic recombination technology. In one embodiment, the term "recombinant human SMN protein" or "rhSMN protein" may refer to human SMN proteins produced, expressed or isolated by recombinant means or genetic recombination technology.

Information regarding the SMN protein and genes encoding the SMN protein is known in the field and the present disclosure is not limited to the SMN protein but may include any polypeptide or protein with one or more activities of the SMN protein described herein. In one embodiment of the present disclosure, the SMN protein may comprise the amino acid sequence of SEQ ID NO: 1, which is based on the sequence of NCBI Accession No. NP_000335.1. In one embodiment, the SMN protein may be encoded by a nucleic acid sequence based on the sequence of NCBI Accession No. NM_000344.4.

In one embodiment, the SMN protein may comprise either the amino acid sequence of SEQ ID NO:1 or an amino acid sequence having homology of at least about 80%, at least about 85%, at least about 90%, at least about 91%, at least about 92%, at least about 93%, at least about 94%, at least about 95%, at least about 96%, at least about 97%, at least about 98% or at least about 99% to the amino acid sequence of SEQ ID NO: 1. In one embodiment, the SMN protein may comprise any protein sequence having homology to the amino acid sequence of SEQ ID NO:1 and having an activity that is the same or substantially the same as, or corresponds to, that of the protein comprising the amino acid sequence of SEQ ID NO:1. In one embodiment, the SMN protein may comprise any amino acid sequence having a deletion, modification, substitution or addition of one or more amino acids, as long as the amino acid sequence has the homology to the amino acid sequence of SEQ ID NO:1, the amino acid sequence has one or more activities of the SMN protein and/or such a modification, substitution or addition does not substantially affect the function of the SMN protein. For example, one or more amino acids may be deleted, modified, substituted, or added for optimization of and/or convenience in the process of expression and extraction of the protein. More specifically, the SMN protein may be further modified, for example, by comprising the Fc region of SEQ ID NO:2 (the hinge, CH2 region and CH3 region of the immunoglobulin gamma-1 heavy chain). In one embodiment of the present disclosure, the SMN protein may be expressed by adding a signal amino acid of SEQ ID NO:3 near the N terminal of the amino acid sequence of SEQ ID NO: 1 and an Fc region of SEQ ID NO:2 near the C terminal of the amino acid sequence of SEQ ID NO: 1, in order to enhance expression and yield of SMN proteins in host cells (e.g., 293F cells).

In the present disclosure, "homology" may refer to, in an amino acid sequence or nucleic acid sequence of a gene encoding a protein, the degree of identity of bases or amino acid residues between two sequences after aligning the two sequences to match as much as possible in a specific comparative region. If the homology between two genes is sufficiently high, the expression products of the two genes may have the same or similar activity. The percentage (%) of said sequence identity may be determined using a publicly known sequence comparison program (e.g., Blast (NCBI)).

In one embodiment of the present application, SMN proteins can be expressed and produced by methods known in the art to which this disclosure pertains. Host cells suitable for expressing and producing proteins described in this disclosure include vertebrate host cells and eukaryotic cells as described herein. The proliferation of vertebrate cells in culture media has become routine technology. Examples of mammal host cell lines include, but are not limited to, monkey kidney cells (CV1), monkey kidney CV1 transformed by SV40 (COS-7), human embryonic kidney cells (293 cells), baby hamster kidney cells (BHK), Chinese Hamster ovarian cells (CHO), mouse Sertoli cells (TM4), African green monkey kidney cells (VERO-76), human cervical carcinoma cells (HELA), dog kidney cells (MDCK), buffalo rat liver cells (BRL 3A), human lung cells (W138), human hepatocytes (Hep G2), mouse breast tumors (MMT 060562), TRI cells, MRC 5 cell, and FS4 cells.

In one embodiment, host cells used to produce the proteins described in the present disclosure can be cultured in various media. Commercially available media, including and not limited to, e.g., Ham F10 medium, minimum essential medium (MEM), RPMI-1640, Dulbecco's Modified Eagle Medium (DMEM) and any other medium used in the art to which this disclosure pertains, may be used for host cell culture. Any of these media may be supplemented with one or more hormones and/or growth factors (e.g., insulin, transferrin or epidermal growth factors), one or more salts (e.g., sodium chloride, calcium, magnesium or phosphate), one or more buffers (e.g., HEPES), one or more nucleotides (e.g., adenosine and thymidine), one or more antibiotics (e.g., Gentamycin™), one or more trace elements, glucose and/or one or more equivalent energy sources, if necessary. Any other essential/auxiliary supplements may also be included in appropriate concentrations known to a person skilled in the art. Other culture conditions, including and not limited to, e.g., temperature, pH and $CO_2$ concentration, can be set to suitable conditions known to a person skilled in the art in relation to host cells selected for protein expression.

In one embodiment, SMN proteins can be included in a pharmaceutical composition, without limitation, at a concentration of about 0.001 to about 500 mg/ml, at a concentration of about 0.01 to about 400 mg/ml, at a concentration of about 0.1 mg to about 300 mg/ml, at a concentration of about 1 mg to about 200 mg/ml, at a concentration of about 1 mg to about 100 mg/ml, at a concentration of about 5 mg to about 70 mg/ml, at a concentration of about 5 mg to about 50 mg/ml, at a concentration of about 10 mg to about 50 mg/ml, at a concentration of about 10 mg to about 30 mg/ml, or at a concentration of about 10 mg to about 20 mg/ml. In one embodiment, SMN proteins can be included in a pharmaceutical composition, without limitation, at a concentration of about 0.001 mg/ml, about 0.01 mg/ml, about 0.1 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 12 mg/ml, about 14 mg/ml, about 15 mg/ml, about 20 mg/ml, about 25 mg/ml, about 30 mg/ml, about 35 mg/ml, about 40 mg/ml, about 45 mg/ml, about 50 mg/ml, about 60 mg/ml, about 70 mg/ml, about 80 mg/ml, about 90 mg/ml, about 100 mg/ml, about 200 mg/ml, about 300 mg/ml, about 400 mg/ml, or about 500 mg/ml, inclusive, including any values in between these numbers.

Pharmaceutical Composition and Treatment of SMA

In one embodiment of the present disclosure, a pharmaceutical composition comprising SMN protein can be formulated and administered in a manner consistent with medical and clinical practice. Factors considered in this regard include, but are not limited to, the disease being treated, the specific animal being treated, the clinical condition of an individual subject, the cause of the disease, the delivery site of the substance, the method of administration, the administration plan, and other factors known to clinicians. In one embodiment, formulations of the pharmaceutical composition may include, but are not limited to, a liquid formulation or a freeze dry powder formulation. In one embodiment, the pharmaceutical composition of the present disclosure can be manufactured in the form of an ampoule, a vial, a bottle, a cartridge, a reservoir, Lyo-Ject® or a pre-filled syringe. In one embodiment, the pharmaceutical composition may be manufactured in a single dosage form or a multiple dosage form.

The terms "pharmaceutically effective dose," "pharmaceutically effective amount," "administration dose," "administration amount," "therapeutically effective dose," "therapeutically effective amount," "effective dose" and/or "effective amount" of the SMN protein administered to a subject refer to the minimum amount required for the prevention, amelioration or treatment of a particular disease (e.g., SMA) and may be determined by the considerations described above. In one embodiment, the terms "pharmaceutically effective dose," "pharmaceutically effective amount," "administration dose," "administration amount," "therapeutically effective dose," "therapeutically effective amount," "effective dose" and/or "effective amount" of the SMN protein may be, but are not limited to, e.g., from about 0.0001 mg/kg to about 150 mg/kg per dose, from about 0.001 mg/kg to about 100 mg/kg per dose from about 0.01 mg/kg to about 50 mg/kg per dose, about 0.05 mg/kg to about 30 mg/kg per dose, about 0.1 mg/kg to about 30 mg/kg per dose, or about 1 mg/kg to about 15 mg/kg per dose; or may be about 0.001 mg/kg per dose, about 0.01 mg/kg per dose, about 0.05 mg/kg per dose, about 0.1 mg/kg per dose, about 0.5 mg/kg per dose, about 1 mg/kg per dose, about 5 mg/kg per dose, about 10 mg/kg per dose, about 15 mg/kg per dose, about 20 mg/kg per dose, about 25 mg/kg per dose, about 30 mg/kg per dose, about 35 mg/kg per dose, about 40 mg/kg per dose, about 45 mg/kg per dose, about 50 mg/kg per dose, about 55 mg/kg per dose, about 60 mg/kg per dose, about 70 mg/kg per dose, about 80 mg/kg per dose, about 90 mg/kg per dose, about 100 mg/kg per dose or about 150 mg/kg per dose, inclusive, including any values in between these numbers. Accordingly, the pharmaceutical composition of the present disclosure may include from about 0.001 mg, about 0.01 mg, about 0.05 mg, about 0.1 mg, about 0.5 mg, about 1 mg, about 5 mg, about 10 mg, about 15 mg, about 30 mg, about 50 mg, about 100 mg, about 200 mg, about 300 mg, about 400 mg, about 500 mg, about 600 mg, about 700 mg, about 800 mg, about 900 mg or about 1000 mg of SMN protein in a single dose, inclusive, including any values in between these numbers. The pharmaceutical composition of the present disclosure may be administered periodically (including but not limited to, e.g., once a day, three times a week, twice a week, once a week, once every two weeks, three times a month, twice a month or once a month), depending on the judgment of an experienced clinical practitioner, and may be administered non-periodically in situations including but not limited to, e.g., acute progression of the disease.

In one embodiment, the pharmaceutical composition of the present disclosure may be administered to a subject in combination with one or more existing SMA therapies. For example, the pharmaceutical composition may be administered in combination with an approved drug, SPINRAZA®, ZOLGENSMA® and/or EVRYSDI®. In one embodiment, a combination is provided as a simultaneous administration, wherein SMN protein and at least one approved drug is administered together in the same composition or administered simultaneously in different compositions. In one embodiment, a combination is provided as a separate administration, wherein the administration of SMN protein can occur prior to, simultaneously, and/or following administration of at least one approved drug. The interval between sequential administration can be in terms of at least (or, alternatively, less than) minutes, hours, or days.

In one embodiment of the present application, the pharmaceutical composition of the present disclosure may be prepared using standard methods known to a person skilled in the art by, e.g., mixing an SMN protein with a desired degree of purity with a pharmaceutically or physiologically acceptable carrier, excipient or stabilizer. In one embodiment, an acceptable carrier includes, but is not limited to, e.g., saline or buffer, such as phosphate, citrate and other organic acids; antioxidant, e.g., ascorbic acid; a low molecular weight polypeptide (including less than about 10 amino acid residues); protein, e.g., serum albumin, gelatin or immunoglobulin; hydrophilic polymer, e.g. polyvinylpyrrolidone; amino acid, e.g., glycine, glutamine, asparagine, arginine or lysine; monosaccharide, disaccharide and other carbohydrate, e.g., glucose, mannose or dextrin; chelating agent, e.g., EDTA; sugar alcohol, e.g., mannitol or sorbitol; salt-forming counter-ions, e.g., sodium; and/or non-ionic surfactants, e.g., TWEEN™, PLURONICS™ or PEG.

In one embodiment, the pharmaceutical composition of the present disclosure may contain a pharmaceutically acceptable salt in an approximately physiological concentration. Optionally, a formulation of the pharmaceutical composition according to one embodiment of the present disclosure may contain a pharmaceutically acceptable preservative. Specifically, in one embodiment, the preservative concentration may be from about 0.1% to about 2.0% (typically v/v). In one embodiment, the preservative may be a preservative generally known in the pharmaceutical industry, and specifically the preservative may be, but is not limited to, e.g., benzyl alcohol, phenol, m-cresol, methylparaben, propylparaben or any combination thereof. In one embodiment, the pharmaceutical composition may contain a pharmaceutically acceptable surfactant. Specifically, in one embodiment, the surfactant concentration may be from about 0.005% to about 0.02%.

In one embodiment of the present disclosure, SMN protein, or a pharmaceutical composition comprising the same may be administered to a subject via either ICV, IT, ICM, intraparenchymal, IC, IV administration or a combination thereof. For ICV, IT, ICM, intraparenchymal, IC or IV administration, one or more methods generally known in the art of the present disclosure may be used.

In one embodiment, the administration of SMN protein or the pharmaceutical composition comprising the same may be performed via an intraventricular catheter system, which comprises a reservoir and a catheter connected to the reservoir. In the following examples, the pharmaceutical composition was administered to mice, so a separate stereotactic device and a stereotactic coordinate system were required. However, in a clinical setting, the SMIN protein or the pharmaceutical composition of the present disclosure may be administered via an intraventricular catheter system.

In one embodiment, an administration of the pharmaceutical composition may comprise the steps of: 1) surgically inserting a catheter system, wherein a reservoir is located under the subject's scalp, wherein the end of the catheter is located within the subject's cerebral ventricle (e.g., lateral ventricle) such that an interior space of any one of cerebral ventricles is connected to an interior space of the reservoir through an interior space of the catheter, and wherein cerebrospinal fluid flows from the cerebral ventricle into the reservoir to fill the reservoir; 2) drawing from about 0.1 to about 5 ml of cerebrospinal fluid from the reservoir, at a rate of about 0.1 to about 60 ml/minute; 3) injecting from about 0.1 to about 5 ml of the pharmaceutical composition into the reservoir, at a rate of about 0.1 to about 60 ml/minute; and 4) allowing the pharmaceutical composition to flow through the catheter from the reservoir into the cerebral ventricle.

In one embodiment, a subject in need of treatment may have an intraventricular catheter system with a reservoir and a catheter (e.g., an Ommaya reservoir) that is implanted for ICV administration. In one embodiment, ICV administration may be performed by injecting the aforementioned formulation into the reservoir at a flow rate of about 0.1 to about 60 ml/minute. In one embodiment, the subject's cerebrospinal fluid (CSF) is discharged at a flow rate of about 0.1 to about 60 ml/minute from the reservoir prior to the ICV administration of the formulation, so that there is no overall increase in the CSF volume of the subject after the ICV administration, thereby preventing an increase in intracranial pressure. In one embodiment, the formulation injected into the reservoir may be transferred through the catheter into the subject's ventricle by slightly compressing and releasing the reservoir.

One embodiment of the present disclosure may be directed to a method for treating, preventing or ameliorating SMA, comprising ICV, IT, ICM, intraparenchymal, IC and/or IV administration of SMN protein.

One embodiment of the present disclosure may be directed to the use of SMN protein administered ICV, IT, ICM, intraparenchymal, IC and/or IV for the treatment, prevention or amelioration of SMA.

One embodiment of the present disclosure may be directed to SMN protein for use in a method for treating, preventing or ameliorating SMA, or a pharmaceutical composition comprising the same.

Working examples and experimental examples described herein explain the composition and effects of the present disclosure in great details, but these examples are provided for illustrative purposes only, to help understand the present disclosure, and the categories and/or scope of this disclosure are not limited by the examples.

[Example 1] Production and Obtainment of SMN Protein

In order to produce SMN protein, a plasmid optimized for SMN protein expression in 293F cells was prepared from pcDNA3.1 plasmid as a backbone. Accordingly, a plasmid expressing SMN protein comprising the amino acid sequence of SEQ ID NO:1 was prepared.

In the present example, SMN protein having the signal amino acid sequence near its N terminal and the Fc region near its C terminal, was expressed. The signal amino acid sequence of SEQ ID NO:3 was added near the N terminal of SMN protein for optimization of expression and yield, and the Fc region of SEQ ID NO:2 (hinge, CH2 and CH3 of immunoglobulin gamma-1 heavy chain) was added near the C terminal of SMN protein for identification and obtainment of the protein. The sequence of the rhSMN protein obtained is the amino acid sequence of SEQ ID NO:4.

A plasmid for final protein production comprises (1) BamHI and EcoRI restriction enzyme recognition sites and (2) a nucleic acid sequence for expression of SMA protein located between the BamHI and EcoRI restriction enzyme recognition sites, and (1) and (2) comprise the nucleic acid sequence of SEQ ID NO:5. In the nucleic acid sequence of SEQ ID NO:5, the nucleotides at positions 1-6 refer to a sequence of BamHI restriction enzyme recognition site, the nucleotides at positions 7-12 refer to Kozak sequence and the nucleotides at positions 1654-1659 refer to a sequence of EcoRI restriction enzyme recognition site. From the nucleic acid sequence of SEQ ID NO:5, recombinant SMN protein having the amino acid sequence of SEQ ID NO:6 was expressed.

Figure 2:
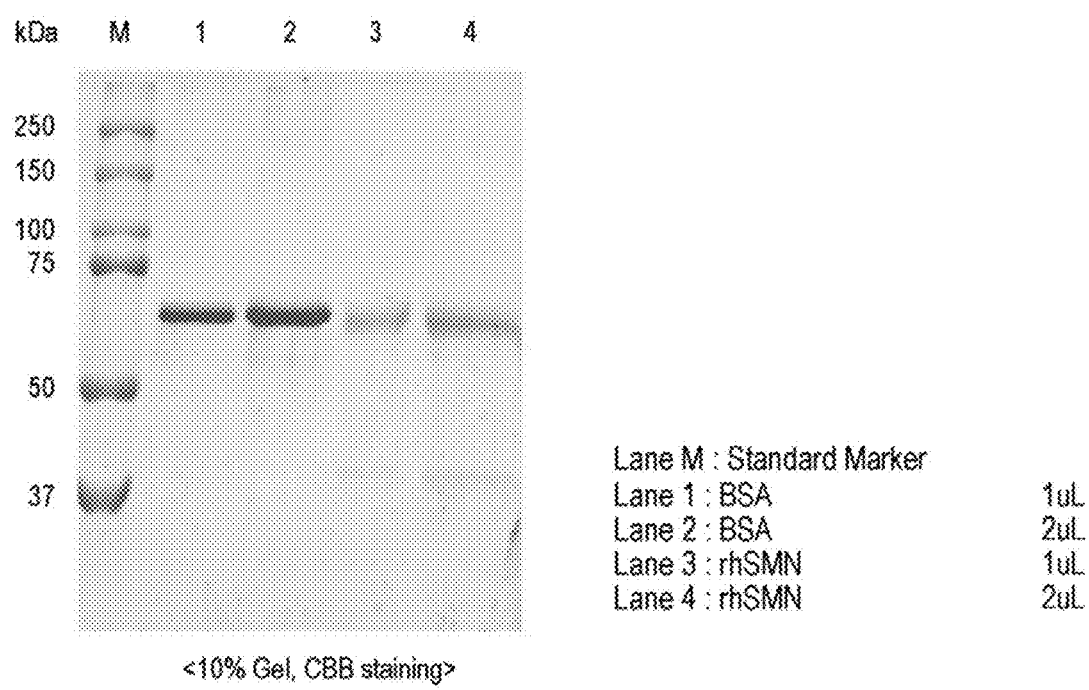
FIG. 2 shows the SDS-PAGE result (10% gel) of rhSMN protein purified with Protein A resin.

The plasmid prepared as described above was transformed into 239F cells with polyethyleneimine. The cells were then cultured for 6 days at a temperature of 37° C. and a $CO_2$ concentration of 8%, to express and obtain the rhSMN protein. On the sixth day of incubation, the Western blot was conducted on the supernatant of cell culture to confirm the expression of rhSMN protein (FIG. 1). Like the control group (Control_Fc), which showed a band corresponding to Fc protein, the cell culture supernatant for cells expressing rhSMN protein clearly showed a band corresponding to the rhSMN protein. The rhSMN protein in the supernatant of cell culture was purified using the Protein A Resin. The protein was dyed with Coomassie Brilliant Blue (CBB), and SDS-PAGE was conducted on a 10% gel to measure the purity of the rhSMN protein (FIG. 2). The concentration of the manufactured protein was measured to be 1.66 mg/mL. The rhSMN protein manufactured as described above was concentrated and used in the example below. The manufacturing of the rhSMN protein was conducted by AbClon Inc.

[Example 2] Administration of SMN Protein in SMA Mouse Model

The rhSMN protein produced in the above Example 1 was administered to a SMA mouse model to confirm the protein's therapeutic effects.

Animals

A mouse model named "Smn allele C" (mouse strain: B6.129-Smn1$^{tm5(smn1/SMN2)Mrph}$/J Osborne, M. et al., *Characterization of behavioral and neuromuscular junction phenotypes in a novel allelic series of SMA mouse models*, Hum Mol Genet 21(20):4431-47) (common name: Smnl$^c$) was purchased from Jackson Laboratory (USA) and used as described below.

Study Design

The administration schedule and the number of mice for each group for the experiment are shown in Table 1 below. Nusinersen is a medicine marketed as SPINRAZA® by Biogen.

Specifically, 2 µL of each administration composition was administered ICV to mice of postnatal day 1. On postnatal day 4, the toes of the mice were marked for identification, and genotyping was performed by sampling the toes of the mice. Only homozygous mutants, identified through genotyping, were selected, and on postnatal day 8, an additional 5 µL of each administration composition was administered ICV.

Tail length and ear necrosis were observed visually to study the effects of the compositions for administration. Tail length was observed at least twice a week from postnatal day 4, and ear necrosis was observed at least twice a week from postnatal week 7.

TABLE 1

Administration schedule and the number of mice

| Group | Administration Composition | Administration Schedule | | # of mice |
|---|---|---|---|---|
| | | Postnatal day 1 | Postnatal day 8 | |
| Negative control group | Carrier (Saline) | 2 µL | 5 µL | 12 |
| Experimental group | rhSMN (5.02 mg/mL) | 10.04 µg/2 µL | 25.1 µg/5 µL | 10 |
| Positive control group | Nusinersen (2.4 mg/ml) | 4.8 µg/2 µL | 12 µg/5 µL | 5-8 |

ICV Administration

ICV administration was performed on mice of postnatal days 1 and 8 as follows.

On the day of administration, a mouse was anesthetized with isoflurane (Hana Pharm Co., Ltd., South Korea) and fixed in a stereotactic instrument (Stoelting, USA). The administration on postnatal day 1 was performed on mice without any additional surgical procedure. On postnatal day 8, the administration was performed on mice, after the skin of the mouse head was minimally peeled off so that the skull was exposed and washed. The administration composition as described in Table 1 above was placed in a single-use plastic syringe, and ICV administration was performed using a syringe pump (KD Scientific, Switzerland) with a 31-gauge needle at a constant rate of 10 µL/minute. The location of a syringe needle in the mouse brain during administration was monitored using stereotaxic coordinates (Stoelting, USA). The coordinates of the needle upon administration were as follows: 0.58 mm caudal to bregma, 1.25 mm lateral to sagittal suture, and 1.77 mm deep.

Vascular rupture or facial edema was monitored at the administration site. Then, the plunger motion was stopped, and the needle was removed after 15 seconds to prevent backflow. The incision was sutured with wound closure clips, and the mouse was placed on an isothermal pad at 37° C. and observed until recovery after surgery. The administration process took about 10 to 15 minutes for about the entire protocol per mouse. The exposed skin area, including the injection site, was briefly sutured with a medical stapler after administration.

Figure 3:
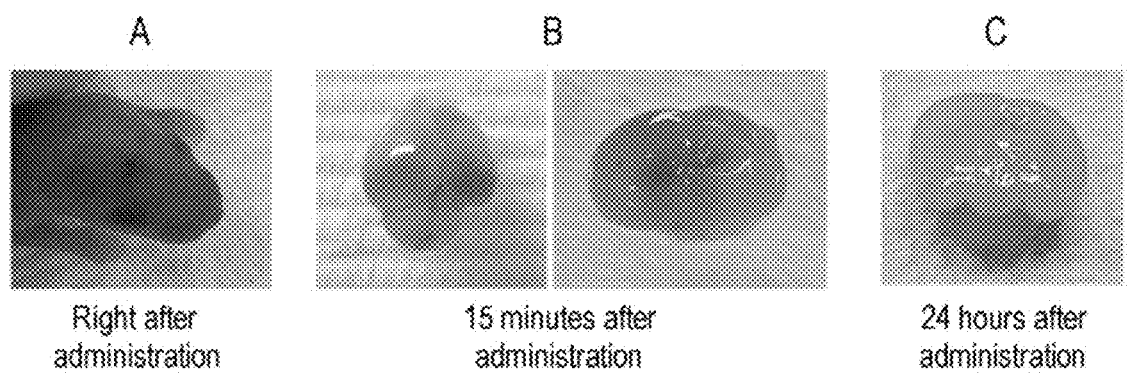
FIG. 3 shows pictures of Trypan Blue delivered and distributed to a brain of a mouse suffering from SMA over time after being administered ICV. More specifically.

In order to determine whether the above ICV administration was successfully performed, the dye solution was administered ICV in the same way as above. Specifically, 0.05% Trypan Blue was administered ICV in the same manner as above, and the brain was collected at each of different time points (i.e., 15 minutes and 24 hours after administration) to visually confirm the distribution of the administration composition. As shown in FIG. 3, after Trypan blue was administered to the cerebral ventricle, it was visually confirmed that the dye solution (and thus the administration composition) spread throughout the brain 15 minutes after administration, and the dye solution (and thus the administration composition) was cleared 24 hours after administration. From this, the ICV administration described above is shown to be a method by which drugs are effectively administered to the mouse brain.

Results

Figure 4:
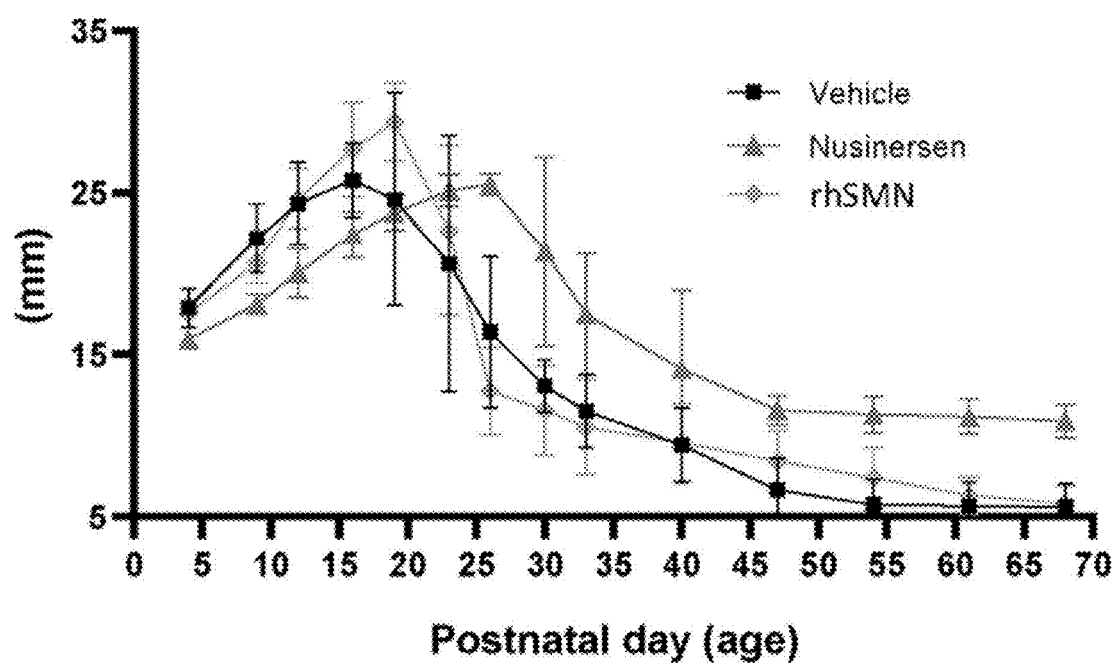
FIG. 4 shows the measurement results of a change in tail length of mice with SMA over time (i.e., the number of postnatal days). More specifically.
Figure 5:
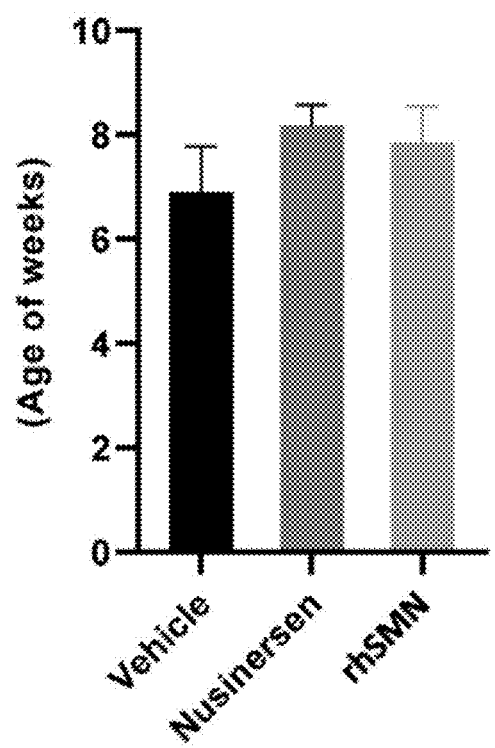
FIG. 5 shows the timing of ear necrosis occurrence in SMA mice (in weeks of age). More specifically.

Observations of tail length and ear necrosis are shown in FIGS. 4, 5 and 6. According to FIG. 4, in the experimental group where rhSMN protein was administered ICV, the SMA symptom of shortened tail is delayed or improved compared to the negative control group that was not administered with any drug. Specifically, in negative control group, the tail length began to be shortened on postnatal day 16, but in the experimental group, the tail length began to be shortened on postnatal day 19.

ICV administration of rhSMN protein was shown to delay or improve the shortening of tail length to the equivalent degree to the positive control group. In the experimental group, the effect of delaying the shortening of tail length after administration of rhSMN protein appeared at a relatively early stage and then disappeared quickly, while in the positive control group, the effect after administration was relatively slow and decreased slowly. This phenomenon is understood to be due to different properties of the administration compositions. In the experimental group, rhSMN protein is administered in the body and acts immediately as a final active ingredient without a separate expression process, while in the positive control group, Nusinersen acts on the expression of SMN2 mRNA in the body. Therefore, if SMN protein and Nusinersen are administered in combination, the two drugs would work in a complementary manner to each other and more effectively treat or prevent SMA or delay, improve or ameliorate its symptoms. In addition, in the experimental group, the effect of the administration composition decreases rapidly due to protein clearance, so the effect is expected to continue when administered every two weeks.

According to FIGS. 5 and 6, in the experimental group where rhSMN protein was administered ICV, the timing of occurrence of ear necrosis was delayed compared to the negative control group where no drug was administered, and this effect was equivalent to that of the positive control group. Specifically, in the negative control group, ear necrosis appeared in postnatal week 7, but in the experimental group and the positive control group, ear necrosis began in postnatal week 8.

From the above descriptions, a person skilled in the art to which the present disclosure pertains will understand that the present disclosure can be practiced in other specific forms without changing its technical idea or essential features. In this regard, it is understood that the examples described above are exemplary and not limiting in all respects. The scope of the present disclosure is construed so as to include the meaning and scope of the claims and all modifications, alterations or alternatives derived from the present disclosure and its equivalent concepts.

SEQUENCE LISTING

```
Sequence total quantity: 6
SEQ ID NO: 1              moltype = AA   length = 294
FEATURE                   Location/Qualifiers
source                    1..294
                          mol_type = protein
                          organism = Homo sapiens
SEQUENCE: 1
MAMSSGGSGG GVPEQEDSVL FRRGTGQSDD SDIWDDTALI KAYDKAVASF KHALKNGDIC    60
ETSGKPKTTP KRKPAKKNKS QKKNTAASLQ QWKVGDKCSA IWSEDGCIYP ATIASIDFKR   120
ETCVVVYTGY GNREEQNLSD LLSPICEVAN NIEQNAQENE NESQVSTDES ENSRSPGNKS   180
DNIKPKSAPW NSFLPPPPPM PGPRLGPGKP GLKFNGPPPP PPPPPHLLS CWLPPFPSGP    240
PIIPPPPPIC PDSLDDADAL GSMLISWYMS GYHTGYYMGF RQNQKEGRCS HSLN         294

SEQ ID NO: 2              moltype = AA   length = 232
FEATURE                   Location/Qualifiers
source                    1..232
                          mol_type = protein
                          organism = synthetic construct
SEQUENCE: 2
EPKSSDKTHT SPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 3              moltype = AA   length = 20
FEATURE                   Location/Qualifiers
source                    1..20
                          mol_type = protein
                          organism = Mus musculus
SIGNAL                    1..20
                          note = Ig kappa chain V-III region MOPC 63
SEQUENCE: 3
METDTLLLWV LLLWVPGSTG                                                20

SEQ ID NO: 4              moltype = AA   length = 526
FEATURE                   Location/Qualifiers
source                    1..526
                          mol_type = protein
                          organism = synthetic construct
SEQUENCE: 4
MAMSSGGSGG GVPEQEDSVL FRRGTGQSDD SDIWDDTALI KAYDKAVASF KHALKNGDIC    60
ETSGKPKTTP KRKPAKKNKS QKKNTAASLQ QWKVGDKCSA IWSEDGCIYP ATIASIDFKR   120
ETCVVVYTGY GNREEQNLSD LLSPICEVAN NIEQNAQENE NESQVSTDES ENSRSPGNKS   180
DNIKPKSAPW NSFLPPPPPM PGPRLGPGKP GLKFNGPPPP PPPPPHLLS CWLPPFPSGP    240
PIIPPPPPIC PDSLDDADAL GSMLISWYMS GYHTGYYMGF RQNQKEGRCS HSLNEPKSSD   300
KTHTSPPCPA PELLGGPSVF LFPPKPKDTL MISRTPEVTC VVVDVSHEDP EVKFNWYVDG   360
VEVHNAKTKP REEQYNSTYR VVSVLTVLHQ DWLNGKEYKC KVSNKALPAP IEKTISKAKG   420
QPREPQVYTL PPSRDELTKN QVSLTCLVKG FYPSDIAVEW ESNGQPENNY KTTPPVLDSD   480
GSFFLYSKLT VDKSRWQQGN VFSCSVMHEA LHNHYTQKSL SLSPGK                  526

SEQ ID NO: 5              moltype = DNA   length = 1659
FEATURE                   Location/Qualifiers
source                    1..1659
                          mol_type = other DNA
                          organism = synthetic construct
sig_peptide               13..73
                          note = Ig kappa chain V-III region MOPC 63
CDS                       13..1653
                          protein_id = 6
                          translation = METDTLLLWVLLLWVPGSTGMAMSSGGSGGGVPEQEDSVLFRRGTG
                          QSDDSDIWDDTALIKAYDKAVASFKHALKNGDICETSGKPKTTPKRKPAKKNSQKKNT
                          AASLQQWKVGDKCSAIWSEDGCIYPATIASIDFKRETCVVVYTGYGNREEQNLSDLLSP
                          ICEVANNIEQNAQENENESQVSTDESENSRSPGNKSDNIKPKSAPWNSFLPPPPPMPGP
                          RLGPGKPGLKFNGPPPPPPPPPHLLSCWLPPFPSGPPIIPPPPPICPDSLDDADALGS
                          MLISWYMSGYHTGYYMGFRQNQKEGRCSHSLNEPKSSDKTHTSPPCPAPELLGGPSVFL
                          FPPKPKDTLMISRTPEVTCVVVDVSHEDPEVKFNWYVDGVEVHNAKTKPREEQYNSTYR
                          VVSVLTVLHQDWLNGKEYKCKVSNKALPAPIEKTISKAKGQPREPQVYTLPPSRDELTK
                          NQVSLTCLVKGFYPSDIAVEWESNGQPENNYKTTPPVLDSDGSFFLYSKLTVDKSRWQQ
                          GNVFSCSVMHEALHNHYTQKSLSLSPGK
SEQUENCE: 5
ggatccgcca ccatggaaac cgatactctg ctgctgtggg tgctgctgct gtgggtgcct    60
gggtcaactg gaatggctat gtcctcaggg ggctctgggg gaggcgtgcc cgagcaggag   120
gactccgtgc tgttccggag aggcaccggc cagtctgacg atagcgacat ctgggacgat   180
acagccctga tcaaggccta cgataaggcc gtggcctcct ttaagcacgc cctgaagaac   240
ggcgacatct gcgagacaag cggcaagccc aagaccacac taagcggaa gccagccaag   300
aagaacaaga gccagaagaa gaatacagca gcctccctgc agcagtggaa agtgggcgac   360
aagtgctctg ccatctggag cgaggatggc tgtatctacc ccgccaccat cgccagcatc   420
gacttcaagc gggagacatg cgtggtggtg tacacaggct atggcaacag agaggagcag   480
```

-continued

```
aatctgtccg atctgctgtc tcctatctgt gaggtggcca acaatatcga gcagaacgcc    540
caggagaacg agaatgagtc ccaggtgtct acagacgaga gcgagaacag ccggagcccc    600
ggaaacaagt ccgataatat caagcccaag agcgcccctt ggaactcctt cctgcccct    660
ccacccccta tgccaggacc aaggctggga ccaggcaagc caggcctgaa gtttaatgga   720
cctccccac ctcctccacc accacctcca cacctgctgt cttgctggct gccacctttc    780
ccaagcggac caccaatcat ccctccacca cctccaatct gtcctgactc cctggacgat   840
gccgatgccc tgggcagcat gctgatctcc tggtacatgt ctggctatca caccggctac   900
tatatgggct ttaggcagaa ccagaaggag ggccgctgct cccactctct gaatgagcct   960
aagagctccg acaagaccca cacatccccc ccttgtcctg caccagagct gctgggagga  1020
ccaagcgtgt tcctgtttcc acccaagccc aaggatacc tgatgatcag ccggacccca  1080
gaggtgacat gcgtggtggt ggacgtgtcc cacgaggacc ccgaggtgaa gtttaactgg  1140
tacgtggacg gcgtggaggt gcacaatgcc aagacaaagc cccgggagga gcagtacaac  1200
tctacctata gagtggtgag cgtgctgaca gtgctgcacc aggattggct gaacggcaag  1260
gagtataagt gcaaggtgtc taataaggcc ctgcccgccc ctatcgagaa gaccatcagc  1320
aaggccaagg gccagcctag ggagccacag gtgtacacac tgcctccatc tcgcgacgag  1380
ctgaccaaga accaggtgag cctgacatgt ctggtgaagg gcttctatcc ttccgacatc  1440
gccgtggagt gggagtctaa tggccagcca gagaacaatt acaagaccac acccctgtg  1500
ctggacagcg atggctcctt cttttctgtat tccaagctga ccgtggacaa gagccggtgg  1560
cagcagggca acgtgttcag ctgttccgtg atgcacgaag cactgcacaa tcactacacc  1620
cagaagtcac tgtcactgag cccagggaaa tgagaattc                          1659

SEQ ID NO: 6              moltype = AA   length = 546
FEATURE                   Location/Qualifiers
source                    1..546
                          mol_type = protein
                          organism = synthetic construct
SIGNAL                    1..20
                          note = Ig kappa chain V-III region MOPC 63
SEQUENCE: 6
METDTLLLWV LLLWVPGSTG MAMSSGGSGG GVPEQEDSVL FRRGTGQSDD SDIWDDTALI     60
KAYDKAVASF KHALKNGDIC ETSGKPKTTP KRKPAKKNKS QKKNTAASLQ QWKVGDKCSA    120
IWSEDGCIYP ATIASIDFKR ETCVVVYTGY GNREEQNLSD LLSPICEVAN NIEQNAQENE    180
NESQVSTDES ENSRSPGNKS DNIKPKSAPW NSFLPPPPPM PGPRLGPGKP GLKFNGPPPP    240
PPPPPPHLLS CWLPPFPSGP PIIPPPPPIC PDSLDDADAL GSMLISWYMS GYHTGYYMGF    300
RQNQKEGRCS HSLNEPKSSD KTHTSPPCPA PELLGGPSVF LFPPKPKDTL MISRTPEVTC    360
VVVDVSHEDP EVKFNWYVDG VEVHNAKTKP REEQYNSTYR VVSVLTVLHQ DWLNGKEYKC    420
KVSNKALPAP IEKTISKAKG QPREPQVYTL PPSRDELTKN QVSLTCLVKG FYPSDIAVEW    480
ESNGQPENNY KTTPPVLDSD GSFFLYSKLT VDKSRWQQGN VFSCSVMHEA LHNHYTQKSL    540
SLSPGK                                                              546
```

The invention claimed is:

1. A method of treating, preventing or ameliorating spinal muscular atrophy (SMA) comprising:
    administering to a patient with SMA a therapeutically effective amount of a pharmaceutical composition comprising a survival motor neuron (SMN) protein via an intracerebroventricular (ICV) administration,
    wherein the SMN protein consists of the amino acid sequence of SEQ ID NO: 1, and
    wherein after the administration of the therapeutically effective amount of the pharmaceutical composition, at least one symptom of SMA is reduced in intensity, severity or frequency, or has delayed onset.

2. The method of claim 1, wherein the SMN protein is a recombinant human SMN protein.

3. The method of claim 1, wherein the patient with SMA is a patient with SMA type I, SMA type II, SMA type III or SMA type IV.

4. The method of claim 1, wherein the ICV administration comprises administering to the patient with SMA the therapeutically effective amount of the pharmaceutical composition in one or more cerebral ventricles.

5. The method of claim 1, wherein the ICV administration comprises administering to the patient with SMA the therapeutically effective amount of the pharmaceutical composition via an intraventricular catheter system comprising a reservoir and a catheter connected to the reservoir.

6. The method of claim 1, wherein administering to the patient with SMA the therapeutically effective amount of the pharmaceutical composition comprises administering to the patient with SMA the therapeutically effective amount of the pharmaceutical composition once a week, once every two weeks, twice a month or once a month.

7. The method of claim 1, wherein administering to the patient with SMA the therapeutically effective amount of the pharmaceutical composition comprises administering to the patient with SMA the pharmaceutical composition in a dose of about 0.0001 mg/kg to about 150 mg/kg.

8. The method of claim 1, wherein the pharmaceutical composition is administered in combination with Nusinersen.

* * * * *